(12) United States Patent
Ziehe

(10) Patent No.: US 7,718,834 B2
(45) Date of Patent: May 18, 2010

(54) METHOD FOR THE PRODUCTION OF PRIMARY LONG-CHAIN ALCOHOLS

(76) Inventor: Holger Ziehe, 25S24, Itzehoe (DE)

( * ) Notice: Subject to any disclaimer, the term of this patent is extended or adjusted under 35 U.S.C. 154(b) by 0 days.

(21) Appl. No.: 11/630,560

(22) PCT Filed: Jun. 22, 2005

(86) PCT No.: PCT/DE2005/001117

§ 371 (c)(1), (2), (4) Date: Jan. 24, 2008

(87) PCT Pub. No.: WO2005/123639

PCT Pub. Date: Dec. 29, 2005

(65) Prior Publication Data

US 2008/0293977 A1    Nov. 27, 2008

(30) Foreign Application Priority Data

Jun. 22, 2004    (DE) ................ 10 2004 030 080

(51) Int. Cl.
*C07C 27/00* (2006.01)
*C07C 29/04* (2006.01)

(52) U.S. Cl. ................ 568/911; 568/851; 568/886; 568/910

(58) Field of Classification Search ................ 568/911, 568/851, 886, 910
See application file for complete search history.

(56) References Cited

U.S. PATENT DOCUMENTS 3,775,456 A    11/1973   Acciarri et al.
5,233,103 A  *  8/1993   Lin et al. .................... 568/911

FOREIGN PATENT DOCUMENTS

| CA | 786392  | 5/1968 |
| DE | 1232937 | 1/1967 |
| EP | 0577020 | 1/1994 |

* cited by examiner

*Primary Examiner*—Elvis O Price

(57) ABSTRACT

A method for preparing linear long chain fatty alcohols having 20 to 40 carbon atoms by a growth reaction of ethylene on aluminum compounds.

41 Claims, 1 Drawing Sheet

METHOD FOR THE PRODUCTION OF PRIMARY LONG-CHAIN ALCOHOLS

CROSS REFERENCE TO RELATED APPLICATIONS

Figure 1:
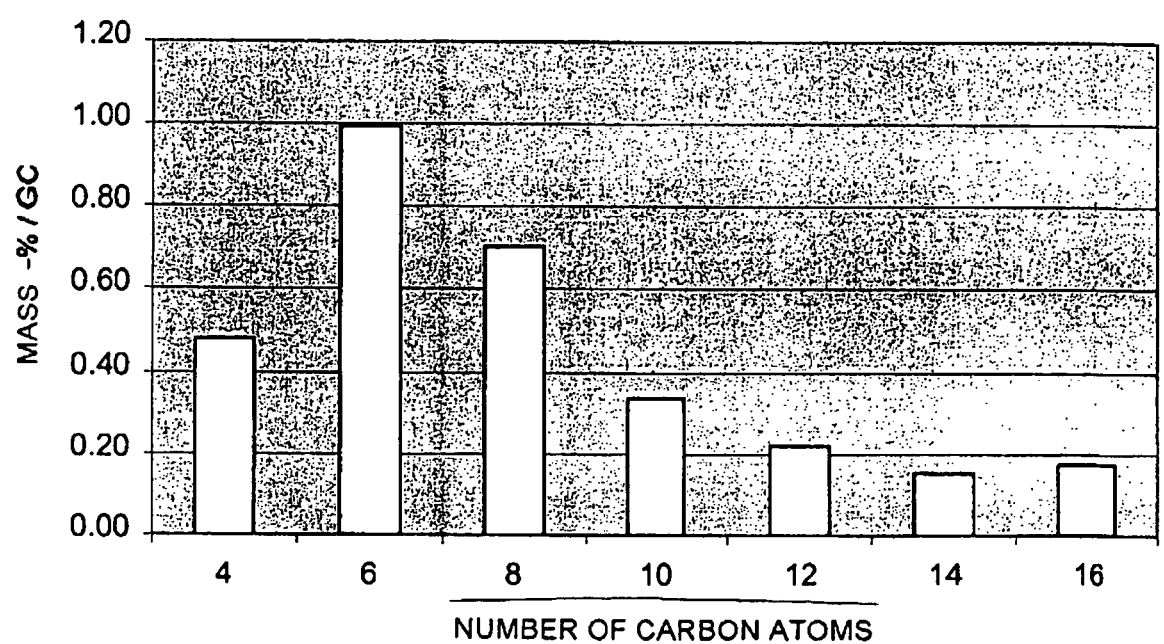

This application claims priority from DE 10 2004 030 080.1 dated Jun. 22, 2004 incorporated herein by reference.

BACKGROUND OF THE INVENTION

1. Field of the Invention

Subject matter of the invention is a method for preparing primary long-chain alcohols having on average greater than 20 carbon atoms.

2. Description of the Prior Art

Behenyl alcohol is a linear long-chain fatty alcohol of the formula $C_{22}H_{45}OH$, however, fatty alcohol mixtures having a chain length range of $C_{18}$ (octadecanol) to $C_{22}$ (docosanol) are also referred to as behenyl alcohols. On an industrial scale, these are prepared by means of fatty acid or fatty acid ester high-pressure hydrogenation. Raw materials for this are in particular erucic, crambe, or fish fatty acid, or their esters, which are obtained by hydrolysis or transesterification of the respective fats. One disadvantage of this method lies in the fact that raw materials from natural sources always provide fatty acid mixtures, consequently, as a matter of principle, the preparation of a certain individual component is coupled to the presence of additional components. Furthermore, this method is limited to chain lengths up to $C_{22}$, with a few exceptions, due to the natural availability of the fatty acids.

According to another method, fatty alcohols are obtainable in the chain length range of $C_{20}$ to $C_{34}$ in accordance with US 2002/0099099-A1. Here, the fatty alcohol mixtures are obtained from natural products, preferably beeswax, by extraction and purification in organic solvents. Alcohol yields of at most 10 to 15% may be obtained if the esters contained in the beeswax are saponified prior to extraction.

Long-chain fatty alcohols up to a chain length of approximately $C_{30}$ are also produced on an industrial scale by means of Ziegler's method (H. Ridder, K. Noweck, Ullmann's Encyclopedia of Industrial Chemistry, Fatty Alcohols, Fifth Edition, Vol. A10, 277-296 (1987)) starting from aluminum, hydrogen, and ethylene. Here, triethylaluminum is subjected with ethylene to a growth reaction, by which is meant the stepwise insertion of ethylene into the aluminum alkyl group; and after oxidation to the aluminum alkoxide and hydrolysis, $C_2$ to $C_{30}$ fatty alcohol mixtures are obtained, the fatty alcohols being present in Poissons's distribution. In methods carried out on an industrial scale, the distribution curve has a maximum at $C_{10}$ to $C_{12}$; however, it can be shifted to lower or higher mean molecular weights through the amount of ethylene used. The raw alcohols are subsequently distilled and separated into mixtures or individual fractions up to a chain length of $C_{18}$ and $C_{20}$, respectively. The portion accumulating in the bottom during distillation contains an alcohol distribution with a maximum at $C_{20}$ and an alcohol content of approximately 80 wt %, or a maximum at $C_{22}$ with an alcohol content of approximately 65 wt %. The raw alcohol obtained with Ziegler's method contains impurities, such as for example paraffins, olefins, ethers, esters, and aldehydes.

According to U.S. Pat. No. 3,255,256, alcohol mixtures, such as for example obtained in Ziegler's process after oxidation and hydrolysis, are converted to aluminum alkoxides in order to then separate the more volatile impurities by distillation or stripping. In this manner, paraffins, olefins, ethers, esters, and aldehydes are successfully separated from alcohols up to a chain length, above which, due to the high boiling points of the secondary components, a thermal decomposition of the alkoxide takes place. The subsequent hydrolysis of the aluminum alcoholates with aqueous systems yields a raw alcohol mixture and aluminum hydroxide.

This method is applicable for the separation of the non-alcoholic secondary components of Ziegler's method; however, it is not suitable for the separation of linear alcohols from branched alcohols. Ziegler raw alcohol contains with growing chains length also an increasing content of predominantly 2-branched alcohols. Analysis of the alcohol fraction of a typical Ziegler alcohol (NAFOL® 20+) after separation using column chromatography gives for example at a chain length of $C_{20}$ 7.8%, at $C_{22}$ 8.0%, and at $C_{24}$ already 17% of branched alcohols (Table 1).

TABLE 1

Example of an Alcohol Distribution of the Alcohol Fraction in NAFOL ® 20+

| Chain Length | Name of n-Alcohol | n-Alcohol Mass-[%] | iso-Alcohol Mass-[%] | Relative Proportion iso-Alcohol [%] |
|---|---|---|---|---|
| $C_{18}$ | Octadecanol | 2 | 0 < 0.1% | — |
| $C_{20}$ | Eicosanol | 40.4 | 3.4 | 7.8 |
| $C_{22}$ | Docosanol | 28.7 | 2.5 | 8.0 |
| $C_{24}$ | Tetracosanol | 8.8 | 1.8 | 17.0 |
| $C_{26}$ | Hexacosanol | 4.3 | 1.2 | 21.8 |
| $C_{28}$ | Octacosanol | 2.1 | 0.9 | 30.0 |
| $C_{30}$ | Triacontanol | 1.0 | 0.6 | 37.5 |
| $C_{32}$ | Dotriacontanol | 0.5 | 0.3 | 37.5 |
| Total | | 87.8 | 10.7 | 10.9 |

During the growth reaction in Ziegler's process, ethylene is stepwise inserted into the aluminum carbon bond of the aluminum alkyls. Starting with triethylaluminum, longer chain aluminum alkyls with an even number of carbons are formed. One of the side reactions is the thermal cleavage of α-olefins, preferably $\geq C_4$, with simultaneous formation of a dialkylaluminum hydride. The olefin cleavage is an equilibrium reaction, i.e., the dialkylaluminum hydride, in turn, can react with ethylene or the α-olefins with chain lengths of $\geq C_4$ to form a trialkylaluminum. Just as in the growth reaction with ethylene, the formed α-olefins can also insert into the aluminum carbon bond. This hydroaluminization reaction takes place regioselectively, preferably with formation of a 2-alkyl-branched ligand which in turn is cleaved off forming a branched olefin. Branched ligands that are bound to the aluminum may also continue to grow with ethylene to longer chains, the branching site then removing itself by two carbon atoms at a time from the aluminum atom.

SUMMARY OF THE INVENTION

It is the object of the present invention to provide a method for preparing linear long-chain alcohols of the formula R—OH, R being a linear alkyl residue $C_nH_{2n+1}$, with $n \geq 20$, preferably 20 to 40, that overcomes the disadvantages of the state of the art and provides both individual fractions and alcohol mixtures with high linearity, a narrow distribution, and high purity in good yields.

In accordance with the invention, the object is solved by a method for preparing linear long-chain fatty alcohols or fatty alcohol mixtures according to claim 1. In detail, the invention relates to a method for preparing primary long-chain alcohols or mixtures thereof having on average n carbon atoms, n being greater than or equal to 20, preferably 20 to 40, in a growth reaction, the method comprising the following steps:

(a) providing aluminum compounds as starting compounds of the growth reaction, each having at least one, preferably two, and more preferably three hydrocarbon residues with at least (n/2+2) carbon atoms, each hydrocarbon residue being bound to the aluminum atom via a primary carbon atom;

(b) subsequent bringing together of the starting compounds in a growth composition that optionally contains other aluminum compounds with ethylene for the conversion with ethylene to form at least aluminum compounds as growth compounds, each having, compared to the starting compound, at least one, preferably two, and more preferably three hydrocarbon residues with on average at least z+(n/2+2) carbon atoms, z being greater than or equal to 2;

(c) oxidation of the conversion products with ethylene with oxygen in order to obtain aluminum oxy compounds having at least one hydrocarbon residue that is bound to the aluminum atom via oxygen;

(d) hydrolysis of the aluminum oxy compounds; and separating a composition containing on average (e) alcohols having greater than or equal to 20 carbon atoms, preferably by distillation, in order to obtain compositions having preferably greater than 90 mol % of linear (mono) alcohols that are preferably further distilled in such a way that, with respect to the longest hydrocarbon residue of the starting compounds used having (n/2+2) carbon atoms, compositions of alcohols having on average no more than 2(n/2+2)–4 hydrocarbon atoms are obtained.

DESCRIPTION OF PREFERRED EMBODIMENTS

The method according to the invention is a modified Ziegler method wherein through the selection or addition of suitable starting components for the growth reaction, fewer side products are formed than in the conventional Ziegler process. The side products differ in their physical properties, such as for example boiling point or melting point, from those of the target products and, consequently, may easily be separated by suitable separation stages, for example by distillation or crystallization. Hence, long-chain fatty alcohols are attained that so far could not be obtained in equal purity by Ziegler's method. The aluminum compounds are normally aluminum alkyls.

Surprisingly, it was found that by means of the method according to the invention, the formation of branched alcohols in the chain length range of greater than or equal to 20, preferably up to 40, may be significantly reduced if the starting compounds described in the patent claims are used.

The preparation of the starting compounds for the growth reaction according to the invention may be carried out using aluminum, hydrogen, and a 1-olefin according to the state of the art. While ethylene is used as olefin component for the preparation of triethylaluminum, longer chain olefins or olefin mixtures are used for the preparation of higher aluminum alkyls. Alternatively, the higher aluminum alkyls may be prepared by transalkylation with short chain aluminum alkyls, preferably with tri(iso-butyl)aluminum or di(iso-butyl)aluminum hydride, or by addition of olefins to di(n-alkyl) aluminum hydride, an intermediate of the trialkylaluminum preparation. The side products of the trialkylaluminum preparation, in particular inert components and/or activators from metallic aluminum, may be separated by distillation or filtration; the side products of the transalkylation, in particular dimeric olefins, may be separated by means of crystallization.

The growth reaction according to the invention may take place both batchwise in a stirred tank reactor and continuously, for example in a stream tube, in the presence or absence of solvent by pressing-on of ethylene. Preferably, one operates in a temperature range of 100 to 130° C. and with a pressure of 20 to 120 bar. After oxidation of the aluminum alkyls with oxygen or oxygen-containing gas mixtures in the presence or absence of catalysts and subsequent hydrolysis with aqueous systems, for example diluted acid, after phase separation, a fatty alcohol raw product is obtained that—if necessary—may be separated, preferably by distillation, into individual alcohol fractions or alcohol mixtures.

In accordance with an additional option, the long-chain olefins that are formed thermally as side products of the growth reaction, predominantly α-olefins, may be bound to the aluminum atom, prior to oxidation, by conversion with short-chain aluminum alkyls, for example tri(iso-butyl)aluminum, di(iso-butyl)aluminum hydride, or long-chain di(n-alkyl)aluminum hydride by means of ligand exchange, or by addition reactions. This conversion occurs thermally, preferably with continuous discharge of the short-chain ligands, and increases the total yield of the long-chain 1-alcohols.

According to another additional option, through conversion, the long-chain, thermally formed 1-olefins are bound to short-chain aluminum alkyls by not additionally adding them, but carrying out an "in-situ" exchange with the already present short-chain aluminum alkyls, while the short-chain olefins are continuously discharged. This exchange is preferably carried out in a distillation or stripping column. The ligand exchange results in the end product in a shift of the alcohol distribution to longer chain alcohols.

In order to clarify the method according to the invention, in the following, the growth reaction on tri(octadecyl)aluminum with ethylene is described as an example, in a manner that allows generalization to other respective educts, that after oxidation and hydrolysis results in an alcohol distribution. From direct hydrolysis of the growth product prior to oxidation, a paraffin and olefin distribution is obtained.

1-Octadecene is bound to the aluminum atom in the presence or absence of solvents by ligand exchange reaction with tri(iso-butyl)aluminum, and tri(octadecyl)aluminum is obtained that may first be purified by crystallization, or may also be directly used in the growth reaction with ethylene. The growth reaction takes place at elevated ethylene pressure of preferably 20 to 120 bar and temperatures of preferably 100 to 130° C.

After oxidation with oxygen and hydrolysis with aqueous systems, a raw alcohol mixture with a chain length distribution of predominantly linear $C_{18}$ to $C_{32}$ alcohols is obtained, as side products being detectable almost exclusively 1-olefins and n-paraffins and astonishingly, however, no iso-alcohols in this chain length range. The 1-olefins formed are side products of the growth reaction, while the n-paraffins are formed, for the most part, by hydrolysis of the aluminum alkyls after incomplete oxidation. The product obtained in this manner is a raw product that was not distilled or stripped on the stage of the alkoxide. By stripping of the aluminum alkoxide, the ratio of n/iso-alcohol is not changed; however, the alcohol content is considerably increased.

TABLE 2

| Chain Length | Name of n-Paraffin | n-Paraffin [%] | iso-Paraffin [%] | 1-Olefin [%] | iso-Olefin [%] |
|---|---|---|---|---|---|
| $C_6$ | Hexane | 1.31 | n.d. | 0.11 | n.d. |
| $C_8$ | Octane | 6.85 | n.d. | 2.51 | n.d. |
| $C_{10}$ | Decane | 11.49 | 0.13 | 2.07 | 0.04 |
| $C_{12}$ | Dodecane | 10.27 | 0.10 | 1.17 | 0.04 |

TABLE 2-continued

| Chain Length | Name of n-Paraffin | n-Paraffin [%] | iso-Paraffin [%] | 1-Olefin [%] | iso-Olefin [%] |
|---|---|---|---|---|---|
| $C_{14}$ | Tetradecane | 6.01 | 0.01 | 0.48 | 0.00 |
| $C_{16}$ | Hexadecane | 2.59 | 0.09 | 0.18 | 0.17 |
| $C_{18}$ | Octadecane | 8.59 | 0.65* | 3.35 | 1.96* |
| $C_{20}$ | Eicosane | 11.49 | 0.05 | 2.13 | 0.03 |
| $C_{22}$ | Docosane | 8.97 | 0.02 | 1.03 | 0.03 |
| $C_{24}$ | Tetracosane | 4.71 | 0.02 | 0.39 | 0.01 |
| $C_{26}$ | Hexacosane | 1.86 | 0.01 | 0.13 | 0.01 |
| $C_{28}$ | Octacosane | 0.60 | 0.01 | 0.04 | 0.01 |
| $C_{30}$ | Triacontane | 0.17 | n.d. | 0.01 | n.d. |
| Total | | 74.91 | 1.09 | 13.6 | 2.30 |

*iso-octadecane and iso-octadecene contained in 1-octadecene

Further side products are short-chain products that are formed due to thermal olefin formation in the growth reaction. The cleavage of 1-olefins results in di(alkyl)aluminum hydrides that, in turn, can react with ethylene and subsequent growth reaction to short-chain aluminum alkyls, and hence to short-chain alcohols. These side products are formed in small amounts; however, they can easily be separated from the final product by distillation due to their boiling range.

Mixtures of aluminum alkyls may also be used. A mixture of tri(octyl)aluminum and tri(octadecyl)aluminum, after oxidation and hydrolysis, e.g. results in an alcohol distribution with two maxima. From direct hydrolysis of the growth product prior to oxidation, a paraffin and olefin distribution according to Table 2 is obtained.

In accordance with the other option of the method according to the invention mentioned briefly above, the olefins that are thermally formed during the growth reaction according to the invention may be recovered. For this, the long-chain olefins are bound again to the aluminum through a ligand exchange reaction with short-chain aluminum alkyls, for example tri(iso-butyl)aluminum, and after oxidation and hydrolysis, a raw alcohol mixture having a significantly higher n-alcohol content and a reduced 1-olefin content is obtained.

Heating for too long in the presence of an excess of tri(iso-butyl)aluminum results in an increased aluminum hydride formation and hence, through "in-situ" hydrolysis, to an increased paraffin formation in the oxidation stage. However, an increased hydride content may also be lowered prior to the oxidation stage by adding 1-olefins.

EXAMPLES

1.A Preparation of Tri(octadecyl)aluminum 29.3 g (116 mmol, 90%) of 1-octadecene and 28.87 g (d=0.695 g/mol; 38.7 ml; 38.7 mmol) of a 1-molar tri(iso-butyl)aluminum solution in hexane were mixed under a nitrogen cover in a 150 ml Schlenk vessel, and the hexane was distilled off. The mixture was heated for another 8.25 hours to 125 to 135° C., the gaseous isobutene formed being discharged via a bubble counter. After cooling to 20° C., the tri(octadecyl)aluminum was obtained as a white solid. By means of NMR analysis, based on 100% aluminumalkyl (Al—$\underline{C}H_2$—), 1.5% dialkylaluminum hydride (Al—$\underline{H}$), 2% alpha-(R$\underline{C}H$=$\underline{C}H_2$), and 3.8% internal olefins (R$\underline{H}C$=$C$ $\underline{H}R'$) were measured. The tri(octadecyl)aluminum was diluted with 50 g of toluene and directly used as starting compound for the following growth reaction (1.C).

1.B Crystallization of Tri(octadecyl)aluminum (Optional)

80.0 g of tri(octadecyl)aluminum and 300 ml of pentane were refluxed. Successively, so much pentane was added, until a clear, saturated solution had formed. Subsequently, the solution was cooled to 20° C. The liquid phase on top of the solid was decanted. After re-crystallization by the same method, a white solid was obtained. The analysis of the hydrolyzed product showed an increase in the n-octadecane content from 77.6 to 95.8%. Furthermore, 1.0% of n-hexadecane and 0.5% of n-eicosane were detected.

1.C Growth Reaction on Tri(octadecyl)aluminum with Ethylene 20 ml each of the tri(octadecyl)aluminum solution in toluene prepared in experiment 1.A were provided with 23.8 bar and 35 bar, respectively, of ethylene pressure in 150 ml steel bombs at 20° C., and the bombs were subsequently heated to 116° C. in a roller oven. In the warm state, initially, a pressure of approximately 35 (and 56 bar, respectively) was reached that declined slightly during the reaction due to the ethylene uptake. After progression of the reaction time of 2 to 3 hours and subsequent cooling to approximately 40° C., the steel bomb was relieved of tension in the glove box and one sample each hydrolyzed with 10% sulfuric acid and analyzed.

TABLE 3

Composition# of the Growth Product of Tri(octadecyl)aluminum after subsequent Hydrolysis.

| Chain Length | Name of n-Paraffin | n-Paraffin [%] | iso-Paraffin [%] | 1-Olefin [%] | iso-Olefin [%] |
|---|---|---|---|---|---|
| a) 23.8 bar (cold), 120 min | | | | | |
| $C_{18}$ | Octadecane | 26.39 | 1.71* | 11.83 | 3.74* |
| $C_{20}$ | Eicosane | 22.25 | 0.08 | 5.00 | 0.04 |
| $C_{22}$ | Docosane | 9.99 | 0.02 | 1.46 | 0.04 |
| $C_{24}$ | Tetracosane | 3.02 | 0.01 | 0.33 | 0.01 |
| $C_{26}$ | Hexacosane | 0.69 | n.d. | 0.06 | n.d. |
| $C_{28}$ | Octacosane | 0.13 | n.d. | 0.01 | n.d. |
| $C_{30}$ | Triacontane | 0.02 | n.d. | n.d. | n.d. |
| Total | | 62.49 | 1.82 | 18.69 | 3.83 |
| b) 23.8 bar (cold), 180 min | | | | | |
| $C_{18}$ | Octadecane | 10.19 | 0.92* | 15.83 | 4.13* |
| $C_{20}$ | Eicosane | 13.39 | 0.05 | 10.47 | 0.05 |
| $C_{22}$ | Docosane | 10.60 | 0.03 | 5.01 | 0.05 |
| $C_{24}$ | Tetracosane | 5.71 | 0.03 | 1.89 | 0.02 |
| $C_{26}$ | Hexacosane | 2.33 | 0.01 | 0.58 | 0.01 |
| $C_{28}$ | Octacosane | 0.77 | 0.01 | 0.16 | 0.01 |
| $C_{30}$ | Triacontane | 0.22 | n.d. | 0.04 | n.d. |
| Total | | 43.21 | 1.05 | 33.98 | 4.27 |
| c) 35 bar (cold), 125 min | | | | | |
| $C_{18}$ | Octadecane | 19.31 | 1.25* | 7.52 | 3.95* |
| $C_{20}$ | Eicosane | 22.95 | 0.06 | 3.07 | 0.07 |
| $C_{22}$ | Docosane | 15.63 | 0.02 | 1.33 | 0.03 |
| $C_{24}$ | Tetracosane | 7.12 | n.d. | 0.46 | n.d. |
| $C_{26}$ | Hexacosane | 2.48 | n.d. | 0.15 | n.d. |
| $C_{28}$ | Octacosane | 0.72 | n.d. | 0.04 | n.d. |
| $C_{30}$ | Triacontane | 0.19 | n.d. | 0.01 | n.d. |
| Total | | 68.40 | 1.33 | 12.58 | 4.05 |

TABLE 3-continued

Composition# of the Growth Product of Tri(octadecyl)aluminum after subsequent Hydrolysis.

| Chain Length | Name of n-Paraffin | n-Paraffin [%] | iso-Paraffin [%] | 1-Olefin [%] | iso-Olefin [%] |
|---|---|---|---|---|---|
| | | d) 35 bar (cold), 145 min | | | |
| $C_{18}$ | Octadecane | 13.26 | 1.06* | 8.72 | 4.07* |
| $C_{20}$ | Eicosane | 18.25 | 0.04 | 4.40 | 0.06 |
| $C_{22}$ | Docosane | 15.49 | 0.02 | 2.29 | 0.03 |
| $C_{24}$ | Tetracosane | 9.00 | 0.02 | 1.02 | 0.01 |
| $C_{26}$ | Hexacosane | 4.20 | n.d. | 0.42 | n.d. |
| $C_{28}$ | Octacosane | 1.71 | n.d. | 0.18 | n.d. |
| $C_{30}$ | Triacontane | 0.69 | n.d. | 0.08 | n.d. |
| Total | | 62.60 | 1.14 | 17.11 | 4.17 | without solvent
*contains impurities from 1-octadecene
n.d.: not detected

1.D Conversion of the Growth Product with Tri(iso-butyl)aluminum

To the combined products from experiments 1.C.c and 1.C.d was added 480 mg (0.69 ml) of a 1M solution of tri(iso-butyl)aluminum in hexane, and after distilling off the hexane, it was heated for an additional 5 hours to 130° C. and 3 hours to 110° C. As determined by means of NMR analysis, the α-olefin content (relative to Al—$CH_2$—=100) had dropped from 14.1 to 7.8%. Another 510 mg (0.73 ml) of tri(iso-butyl)aluminum solution was added and it was heated for an additional 4 hours to 130° C. and 1 hour to 110° C. The α-olefin content was now at 4.6% (Table 4).

TABLE 4

Composition# of the Growth Product after Conversion with Tri(iso-butyl)aluminum and subsequent Hydrolysis.

| Chain Length | Name of n-Paraffin | n-Paraffin [%] | iso-Paraffin [%] | 1-Olefin [%] | iso-Olefin [%] |
|---|---|---|---|---|---|
| $C_{18}$ | Octadecane | 22.54 | 2.25* | 1.35 | 2.81* |
| $C_{20}$ | Eicosane | 23.22 | 0.06 | 1.37 | 0.06 |
| $C_{22}$ | Docosane | 16.95 | 0.01 | 0.98 | 0.04 |
| $C_{24}$ | Tetracosane | 8.85 | 0.02 | 0.52 | 0.02 |
| $C_{26}$ | Hexacosane | 3.71 | n.d. | 0.24 | 0.02 |
| $C_{28}$ | Octacosane | 1.38 | n.d. | 0.10 | n.d. |
| $C_{30}$ | Triacontane | 0.50 | n.d. | 0.04 | n.d. |
| Total | | 77.15 | 2.34 | 4.6 | 2.95 |

1.E Growth Reaction on Mixtures of Tri(octyl)aluminum and Tri(octadecyl)aluminum 10 ml of the tri(octadecyl)aluminum solution in toluene prepared in experiment 1.A and 2.5 g of tri(octyl)aluminum in 2.32 g of toluene were filled into a 150 ml steel bomb and the pressure increased with ethylene to 35 bar at 20° C. The bomb was subsequently heated to 116° C. in a roller oven for 140 min. In the warm state, initially, a pressure of approximately 56 bar was reached that declined during the reaction due to the ethylene uptake. After progression of the reaction time and subsequent cooling to approximately 40° C., the steel bomb was relieved of tension in the glove box and one sample hydrolyzed with 10% sulfuric acid and analyzed (Table 5).

TABLE 5

Composition# of the Growth Product of Mixtures of Tri(octyl)aluminum and Tri(octadecyl)aluminum after subsequent Hydrolysis.

| Chain Length | Name of n-Paraffin | n-Paraffin [%] | iso-Paraffin [%] | 1-Olefin [%] | iso-Olefin [%] |
|---|---|---|---|---|---|
| $C_6$ | Hexane | 1.31 | n.d. | 0.11 | n.d. |
| $C_8$ | Octane | 6.85 | n.d. | 2.51 | n.d. |
| $C_{10}$ | Decane | 11.49 | 0.13 | 2.07 | 0.04 |
| $C_{12}$ | Dodecane | 10.27 | 0.10 | 1.17 | 0.04 |
| $C_{14}$ | Tetradecane | 6.01 | 0.01 | 0.48 | 0.00 |
| $C_{16}$ | Hexadecane | 2.59 | 0.09 | 0.18 | 0.17 |
| $C_{18}$ | Octadecane | 8.59 | 0.65* | 3.35 | 1.96* |
| $C_{20}$ | Eicosane | 11.49 | 0.05 | 2.13 | 0.03 |
| $C_{22}$ | Docosane | 8.97 | 0.02 | 1.03 | 0.03 |
| $C_{24}$ | Tetracosane | 4.71 | 0.02 | 0.39 | 0.01 |
| $C_{26}$ | Hexacosane | 1.86 | 0.01 | 0.13 | 0.01 |
| $C_{28}$ | Octacosane | 0.60 | 0.01 | 0.04 | 0.01 |
| $C_{30}$ | Triacontane | 0.17 | n.d. | 0.01 | n.d. |
| Total | | 74.91 | 1.09 | 13.6 | 2.30 |

2.A Oxidation of the Combined Fractions from Experiments 1.C.a and 1.C.b

The combined raw products from experiments 1.C.a and 1.C.b were provided with a nitrogen pre-pressure of 2.1 bar in a 300 ml Parr autoclave. At 30° C. and an agitation speed of 650 rpm, oxygen was metered with a flow rate of 23 ml/min. The pressure increased within 60 min to 4.9 bar, the oxygen feed was stopped, the solution was heated to 50° C. for another 2 hours and subsequently hydrolyzed with 10% sulfuric acid. The product composition presented in Table 6 was obtained.

2.B Oxidation of the Combined Fractions from Experiment 1.D

The raw product from experiment 1.D was provided with a nitrogen pre-pressure of 2.1 bar in a 300 ml Parr autoclave. At 30° C. and an agitation speed of 650 rpm, oxygen was metered with a flow rate of 23 ml/min. After a reaction time of 30 min, 6.6 mg of tetra(iso-propyl)titanate in 0.8 ml of tridecane was added.

TABLE 6

Composition# of the Growth Product after Oxidation and subsequent Hydrolysis

| Chain Length | Name of n-Alcohol | n-Alcohol Mass-[%] | iso-Alcohol Mass-[%] | 1-Olefin [%] | n-Paraffin [%] |
|---|---|---|---|---|---|
| $C_{18}$ | Octadecanol | 12.4 | n.d. | 15.4 | 3.5 |
| $C_{20}$ | Eicosanol | 13.4 | n.d. | 9.1 | 2.9 |
| $C_{22}$ | Docosanol | 7.8 | n.d. | 3.7 | 1.3 |
| $C_{24}$ | Tetracosanol | 3.2 | n.d. | 1.4 | 0.6 |
| $C_{26}$ | Hexacosanol | 1.0 | n.d. | 0.4 | 0.2 |
| $C_{28}$ | Octacosanol | 0.2 | n.d. | 0.1 | 0.08 |
| $C_{30}$ | Triacontanol | 0.05 | n.d. | 0.05 | 0.03 |
| Total | | 38.1 | — | 30.2 | 8.6 |

The pressure increased within 52 min to 5 bar, the oxygen feed was stopped, the solution was heated to 50° C. for another 6 hours and subsequently hydrolyzed with 10% sulfuric acid at 80° C. The product distribution presented in Table 7 was obtained:

TABLE 7

Composition# of the Growth Product after Oxidation and subsequent Hydrolysis

| Chain Length | Name of n-Alcohol | n-Alcohol Mass-[%] | iso-Alcohol Mass-[%] | 1-Olefin* [%] | n-Paraffin* [%] |
|---|---|---|---|---|---|
| $C_{18}$ | Octadecanol | 17.66 | n.d. | 1.87 | 5.83 |
| $C_{20}$ | Eicosanol | 19.46 | n.d. | 1.92 | 3.76 |
| $C_{22}$ | Docosanol | 13.62 | n.d. | 1.41 | 2.40 |
| $C_{24}$ | Tetracosanol | 6.93 | n.d. | 0.81 | 1.25 |
| $C_{26}$ | Hexacosanol | 2.04 | n.d. | 0.40 | 0.56 |
| $C_{28}$ | Octacosanol | 0.48 | n.d. | 0.22 | 0.24 |
| $C_{30}$ | Triacontanol | 0.10 | n.d. | 0.13 | 0.12 |
| Total | | 60.29 | — | 6.67 | 14.16 |

An overview over the side product formation is presented in FIG. 1 (alcohol distribution).

The solvent content was calculated from the gaschromatographical analyses. The designation n. d. (not detected) specifies that the products are not present or are below the detection limit.

The chemicals used were purchased from Aldrich Company and directly used without further purification. The tri(iso-butyl)aluminum is a 1-molar solution in hexane. The 1-octadecene used is of technical grade and has the following composition: 1-octadecene: 90.6 wt %; vinylidene olefins: 4.2 wt %, internal olefins: 2.3 wt %; 1-eicosenes: 0.6 wt %; 1-hexadecenes: 0.4 wt %; other compounds: 1.9 wt %.

The invention claimed is:

1. A method for preparing primary long-chain alcohols or mixtures thereof having on average n carbon atoms, n being greater than or equal to 20, in a growth reaction, the method comprising:
   (a) providing aluminum compounds as starting compounds of the growth reaction, each having at least one hydrocarbon residue with at least (n/2+2) carbon atoms, each hydrocarbon residue being bound to the aluminum atom via a primary carbon atom;
   (b) bringing together the starting compounds in a growth composition containing ethylene for the conversion with ethylene to form at least aluminum compounds as growth compounds, each having, compared to the starting compound, at least one hydrocarbon residue with on average at least z+(n/2+2) carbon atoms, z being greater than or equal to 2;
   (c) oxidizing the growth compounds with oxygen in order to obtain aluminum oxy compounds having at least one hydrocarbon residue that is bound to the aluminum atom via oxygen;
   (d) hydrolyzing of the aluminum oxy compounds; and
   (e) separating a composition containing on average alcohols having greater than or equal to 20 carbon atoms.

2. The method according to claim 1, characterized in that the composition of the starting compounds prior to the growth reaction has in total a content of less than 10 wt %, of 1-olefins having greater than 2 and less than (n/2+2) carbon atoms.

3. The method according to claim 1, characterized in that at least 90% in total of the hydrocarbon residues of the starting and growth compounds having at least (n/2+2) carbon atoms are linear.

4. The method according to claim 1, characterized in that the hydrocarbon residues of the starting and growth compounds having at least (n/2+2) carbon atoms are alkyl residues.

5. The method according to claim 1, characterized in that the composition has after hydrolysis of the aluminum oxy compounds (step (d)), based on all alcohols in the composition, at least 4 wt % of alcohols with more than 20 carbon atoms.

6. The method according to claim 1, characterized in that the alcohols with more than 20 carbon atoms are separated by separating the aqueous phase from the organic phase and/or distillation.

7. The method according to claim 1, characterized in that the content of 1-olefins and/or hydrocarbon residues bound to aluminum in the growth composition that contain fewer than 24 carbon atoms each and are branched is in total less than 5 wt %.

8. The method according to claim 1, characterized in that the starting compounds are prepared by ligand exchange with aluminum alkyls having hydrocarbon residues with 6 or fewer carbon atoms in the presence of at least one linear long-chain α-olefin having at least (n/2+2) carbon atoms.

9. The method according to claim 1, characterized in that the starting compounds are prepared by conversion of aluminum, hydrogen, and at least one linear long-chain α-olefin having at least (n/2+2) carbon atoms.

10. The method according to claim 1, characterized in that the starting compounds are prepared by addition of α-olefins having at least (n/2+2) carbon atoms to an aluminum compound having at least one hydrocarbon residue and at least one hydridically bound hydrogen atom.

11. The method according to claim 1, characterized in that the starting compounds are crystallized prior to being incorporated into the growth composition.

12. The method according to claim 1, characterized in that prior to oxidizing the growth products, the α-olefins having at least (n/2+2) carbon atoms contained in the growth composition are bound to aluminum compounds with cleavage of α-olefins having fewer than (n/2+2) carbon atoms.

13. The method according to claim 12, characterized in that the aluminum compounds that react with cleavage of α-olefins having fewer than (n/2+2) are di(iso C3 to C6 alkyl) aluminum hydride or tri(iso C3 to C6 alkyl)aluminum.

14. The method according to claim 1, characterized in that the aluminum oxy compounds are distilled or stripped prior to hydrolysis in order to remove side products from the product mixture, while the aluminum oxy compounds remain in a bottoms fraction.

15. The method according to claim 1, characterized in that the growth reaction is carried out at temperatures of 100 to 130° C. and a pressure of 20 to 120 bar.

16. The method according to claim 1, characterized in that the separating in accordance with step (e) occurs by distillation, and that by means of distillation, an alcohol fraction is obtained that contains more than 90 mol % of linear alcohols.

17. The method according to claim 1, characterized in that as starting compounds, the aluminum compounds are selected from the group consisting of:
   (I) starting compounds that each have at least one hydrocarbon residue having greater than or equal to 12 carbon atoms for the preparation of an alcohol fraction having on average 20 carbon atoms;
   (II) starting compounds that each have at least one hydrocarbon residue having greater than or equal to 14 carbon atoms for the preparation of an alcohol fraction having on average 20 to 24 carbon atoms;
   (III) starting compounds that each have at least one hydrocarbon residue having greater than or equal to 16 carbon atoms for the preparation of an alcohol fraction having on average 20 to 28 carbon atoms;

(IV) starting compounds that each have at least one hydrocarbon residue having greater than or equal to 18 carbon atoms for the preparation of an alcohol fraction having on average 20 to 32 carbon atoms;

(V) starting compounds that each have at least one hydrocarbon residue having greater than or equal to 20 carbon atoms for the preparation of an alcohol fraction having on average 20 to 36 carbon atoms;

(VI) and mixtures thereof;

and wherein separating in accordance with step (e) occurs by distillation;

an alcohol fraction being obtained by means of said distillation, that contains more than 90 mol % of linear alcohols.

18. The method according to claim 1, characterized in that as starting compounds, the aluminum compounds are selected from the group consisting of:

(II) starting compounds that each have at least one hydrocarbon residue having greater than or equal to 14 carbon atoms for the preparation of an alcohol fraction having on average 22 to 24 carbon atoms;

(III) starting compounds that each have at least one hydrocarbon residue having greater than or equal to 16 carbon atoms for the preparation of an alcohol fraction having on average 26 to 28 carbon atoms;

(IV) starting compounds that each have at least one hydrocarbon residue having greater than or equal to 18 carbon atoms for the preparation of an alcohol fraction having on average 30 to 32 carbon atoms;

(V) starting compounds that each have at least one hydrocarbon residue having greater than or equal to 20 carbon atoms for the preparation of an alcohol fraction having on average 34 to 36 carbon atoms;

(VI) and mixtures thereof;

wherein separating in accordance with step (e) occurs by distillation;

an alcohol fraction being obtained by means of said distillation, that contains more than 90 mol % of linear alcohols.

19. The method according to claim 2, wherein the wt. % of 1-olefins is less than 3 wt. %.

20. The method of claim 5, characterized in that there are at least 6 wt. % of alcohols with more than 20 carbon atoms.

21. The method of claim 16, wherein said alcohol fraction contains more than 95 mol % of linear alcohols.

22. The method of claim 17, wherein there are at least 2 hydrocarbon residues having greater than or equal to 12 carbon atoms.

23. The method of claim 17, wherein there are at least 3 hydrocarbon residues having greater than or equal to 12 carbon atoms.

24. The method of claim 17, wherein there are at least 2 hydrocarbon residues having greater than or equal to 14 carbon atoms.

25. The method of claim 17, wherein there are at least 3 hydrocarbon residues having greater than or equal to 14 carbon atoms.

26. The method of claim 17, wherein there are at least 2 hydrocarbon residues having greater than or equal to 16 carbon atoms.

27. The method of claim 17, wherein there are at least 3 hydrocarbon residues having greater than or equal to 16 carbon atoms.

28. The method of claim 17, wherein there are at least 2 hydrocarbon residues having greater than or equal to 18 carbon atoms.

29. The method of claim 17, wherein there are at least 3 hydrocarbon residues having greater than or equal to 18 carbon atoms.

30. The method of claim 17, wherein there are at least 2 hydrocarbon residues having greater than or equal to 20 carbon atoms.

31. The method of claim 17, wherein there are at least 3 hydrocarbon residues having greater than or equal to 20 carbon atoms.

32. The method of claim 17, wherein said alcohol fraction obtained by distillation contains more than 95 mol % of linear alcohols.

33. The method of claim 18, wherein there are at least 2 hydrocarbon residues having greater than or equal to 14 carbon atoms.

34. The method of claim 18, wherein there are at least 3 hydrocarbon residues having greater than or equal to 14 carbon atoms.

35. The method of claim 18, wherein there are at least 2 hydrocarbon residues having greater than or equal to 16 carbon atoms.

36. The method of claim 18, wherein there are at least 3 hydrocarbon residues having greater than or equal to 16 carbon atoms.

37. The method of claim 18, wherein there are at least 2 hydrocarbon residues having greater than or equal to 18 carbon atoms.

38. The method of claim 18, wherein there are at least 3 hydrocarbon residues having greater than or equal to 18 carbon atoms.

39. The method of claim 18, wherein there are at least 2 hydrocarbon residues having greater than or equal to 20 carbon atoms.

40. The method of claim 18, wherein there are at least 3 hydrocarbon residues having greater than or equal to 20 carbon atoms.

41. The method of claim 18, wherein said alcohol fraction obtained by distillation contains more than 95 mol % of linear alcohols.

* * * * *